(12) United States Patent (10) Patent No.: US 8,715,213 B2
Yamazaki et al. (45) Date of Patent: May 6, 2014

(54) BONE METABOLISM IMPROVING AGENT

(75) Inventors: Hidehiro Yamazaki, Tokyo (JP);
Toshihiro Ohki, Tokyo (JP); Tomio Inaba, Tokyo (JP); Naomi Sakaguchi, Tokyo (JP)

(73) Assignee: Ajinomoto Co., Inc., Tokyo (JP)

( * ) Notice: Subject to any disclaimer, the term of this patent is extended or adjusted under 35 U.S.C. 154(b) by 615 days.

(21) Appl. No.: 12/558,040

(22) Filed: Sep. 11, 2009

(65) Prior Publication Data

US 2010/0056974 A1 Mar. 4, 2010

Related U.S. Application Data

(63) Continuation of application No. PCT/JP2008/054598, filed on Mar. 13, 2008.

(30) Foreign Application Priority Data

Mar. 14, 2007 (JP) ................................. 2007-065660

(51) Int. Cl.
*A61M 37/00* (2006.01)
*C02F 1/44* (2006.01)

(52) U.S. Cl.
USPC ........................ 604/5.04; 210/645; 210/646

(58) Field of Classification Search
USPC .............. 604/4.01, 5.01, 5.04, 6.09; 210/645, 210/646
See application file for complete search history.

(56) References Cited

U.S. PATENT DOCUMENTS 6,080,431 A * 6/2000 Andon et al. ................. 424/602

FOREIGN PATENT DOCUMENTS

| EP | 1 834 652 | 9/2007 | | |
|---|---|---|---|---|
| JP | 2003-104869 | 4/2003 | | |
| JP | 2003339853 A | * 12/2003 | ............. | A61M 1/14 |
| WO | 2006/073164 | 7/2006 | | |

OTHER PUBLICATIONS

JP 2003339853 A, English translation.*
Hruska KA and SL Teitelbaum, Renal Osteodytrophy. N. Engl J Med 1995; 333:166-175 (Jul. 1995).*
Masaru Imai et al, "Low calcium dialysate", *Japanese Journal of Clinical Medicine*, Special Extra Issue in 1991, first volume, Nippon Rinshosha, 1991, pp.295-300.
Masaaki Nakayama et al, "Low calcium dialysate", *Japanese Journal of Clinical Medicine*, Special Extra Issue in 1991, first volume, Nippon Rinshosha, 1991, pp. 527-531.
Ryoichi Nakazawa, "Dialysis bone disease associated with secondary hyperparathyroidism" *Japanese Journal of Clinical Medicine*, Special Extra Issue in 1992, last volume, Nippon Rinshosha, 1992, pp. 783-788.

(Continued)

*Primary Examiner* — Leslie Deak
(74) *Attorney, Agent, or Firm* — Oblon, Spivak, McClelland, Maier & Neustadt, L.L.P.

(57) ABSTRACT

The present invention has as an object to provide a bone metabolism improving agent that improves bone metabolism in a chronic renal failure patient receiving blood purification therapy such as hemodialysis, hemofiltration and hemodiafiltration. An acetic acid- and/or acetate salt-free bone metabolism improving agent that contains citric acid and/or a citrate salt as electrolytes and further contains another/other electrolyte/electrolytes and glucose solely or in combination is provided. A bone metabolism improving agent formulated into a dialysate or a substitution fluid having effects of improving bone metabolism including bone metabolism improvement in adynamic bone disease and especially in bone agenesis is also provided.

20 Claims, 2 Drawing Sheets

Changes in ionized calcium concentration
(After dialysis)

(56) References Cited

OTHER PUBLICATIONS

Satoshi kurihara et al, "Low Turnover Bone Disease in Patients with Chronic Renal Failure", *Clin. Calcium*, 2000, vol. 10, No. 10, pp. 1221-1228.

Robert Apsner et al, "Parathyroid Hormone Secretion During Citrate Anticoagulated Hemodialysis in Acutely Ill Maintenance Hemodialysis Patients", *Anesthesia & Analgesisia*, 2004, vol. 99, No. 4, pp. 1199-1204.

Yoshiko Iwasaki et al, "Jinkino no Teika Mukeiseikotsu eno Iko o Sokushinsuru", *Journal of the Japanese Society for Bone Mineral Research*, 2001, vol. 19, No. 2, p. 140, P-099 (with English translation).

Akira Saito et al, "Multicenter comparative clinical trial of acetate-free dialysate, SZ-D21 (phase III study)", *Medical Consultation & New Remedies (Shindann to Shinyaku)*, Mar. 28, 2007, vol. 44, No. 3, pp. 260-278 (with English translation).

L. Darryl Quarles et al, "Intact Parathyroid Hormone Overestimates the Presence and Severity of Parathyroid-Mediated Osseous Abnormalities in uremia", *Journal of Clinical Endocrinology and Metabolism*, 1992, vol. 75, No. 1, pp. 145-150.

G.A. Coles, "Body Composition in Chronic Renal Failure", *Quarterly Journal of Medicine*, New Series, Jan. 1972, vol. 41, No. 161, pp. 25-47.

William E. Mitch et al, "Mechanisms Activated by Kidney Disease and the Loss of Muscle Mass", *American Journal of Kidney Diseases*, Dec. 2001, vol. 38, No. 6, pp. 1337-1342.

\* cited by examiner

Changes in ionized calcium concentration
(Before dialysis)

Changes in ionized calcium concentration
(After dialysis)

Period using Dialysate of the Invention

Period using Dialysate of the Control

BONE METABOLISM IMPROVING AGENT

CROSS REFERENCES TO RELATED APPLICATIONS

This application is a continuation of International Patent Application No. PCT/JP2008/054598, filed on Mar. 13, 2008, and claims priority to Japanese Patent Application No. JP 2007-065660, filed on Mar. 14, 2007, all of which are incorporated herein by reference in their entireties.

BACKGROUND OF THE INVENTION

1. Field of the Invention

The present invention relates to bone metabolism improving agents that improve bone metabolism in the living body, and more specifically, to a bone metabolism improving agent that improves bone metabolism in a chronic renal failure patient who receives blood purification therapy such as hemodialysis, hemofiltration and hemodiafiltration.

Further, the present invention relates to methods for improving bone metabolism in a chronic renal failure patient who receives blood purification therapy such as hemodialysis, hemofiltration and hemodiafiltration, by administration of above bone metabolism improving agents; and more specifically, to a method for improving bone metabolism employing a dialysate and/or a substitution fluid that contain above bone metabolism improving agents.

Furthermore, the present invention relates to methods for blood purification including hemodialysis and hemodiafiltration in a chronic renal failure patient employing dialysates that contain above bone metabolism improving agents, and additionally to methods for blood purification including hemodiafiltration and hemofiltration in a chronic renal failure patient employing substitution fluids that contain above bone metabolism improving agents.

2. Discussion of the Background

Chronic renal failure patients who receive blood purification therapy, typically hemodialysis, suffer from lowered quality of life (QOL), hospitalization and high mortality rates induced by various complications. It is well known that causes of such complications include chronic inflammatory state, nutritional deficiencies, arteriosclerosis and anemia, and that interrelation among them deteriorates prognosis.

Because kidney plays a key role in conjunction with parathyroid glands, bone and intestinal tract in the intricate controlling system for maintaining calcium (Ca) and phosphorus (P) balances in the living body as well as keeping calcium ion concentrations of extracellular fluid within the physiological range, chronic renal failure with renal function disordered causes various abnormalities. One of such abnormalities is bone metabolism abnormality.

For example, chronic renal failure patients develop hypocalcemia induced by hyperphosphatemia due to lowered phosphorus excretion in the kidney. Renal hypofunction also causes phosphorus retention due to nephron reduction and low blood concentrations of 1α, 25-dihydroxyvitamin D, an activated vitamin D, induced by decreased hydroxylation of 25-hydroxyvitamin D at the 1-alpha position. Decreased blood concentrations of 1α, 25-dihydroxy-vitamin D cause calcium malabsorption at the small intestine as well as low serum calcium concentrations due to decreased bone resorption.

As a result of phosphorus retention, hypocalcemia and vitamin D activation disorder, secretion of parathyroid hormone (PTH) increases for compensation.

Disorder of renal function that plays key roles in controlling calcium and phosphorus concentrations in blood serum and vitamin D activation as mentioned above affects not only bone metabolism itself but also prognosis in the long term due to calcinosis in the blood vessel and whole body.

In renal failure patients, bone reactivity to PTH (bone turnover) is lowered because of phosphorus retention, activated vitamin D deficiency and PTH receptor disorder. According to bone histological findings, the blood PTH concentrations essential for maintaining normal bone turnover (intact PTH: i-PTH concentrations) in a dialysis patient are from 2.5 to 3 times higher than a healthy subject when the rate of osteogenesis is used as an indicator (Non-patent literature 1).

Generally the pathology that bone turnover is decreased with i-PTH concentrations falling below the normal range is called absolute hypoparathyroidism. In contrast, renal failure patients develop the pathology that normal bone turnover is not maintained notwithstanding normal i-PTH concentrations because of decreased bone reactivity to PTH—the pathology called relative hypoparathyroidism. Relative hypoparathyroidism has been considered to be a major cause of bone agenesis.

Thus, it has been assumed significant for improvement of QOL and prognosis of chronic renal failure patients receiving blood purification therapy such as hemodialysis, hemofiltration and hemodiafiltration to improve bone metabolism in adynamic bone disease by correcting blood ionized calcium concentrations. In line with the above, use of dialysis preparations whose calcium concentrations are set lower than general dialysis preparations has been recommended for treatment of adynamic bone disease.

However, use of such low-calcium dialysis preparations in blood purification therapy for a long time causes decreased bone mineral density in the body. As above, there has been developed no truly effective therapeutic agent up to the present.

Chronic renal failure patients also develop retention of water and uremic substances, electrolyte abnormality and metabolic acidosis induced by renal dysfunction. Especially, metabolic acidosis is known to accelerate hypermetabolism of proteins and amino acid (Non-patent literatures 2 and 3). Therefore, a major objective of hemodialysis is correction of blood acid-base balance.

In the early years of hemodialysis history, bicarbonate dialysis preparations that contain sodium hydrogencarbonate (sodium bicarbonate) as an alkalizer were used because sodium hydrogencarbonate is one of components of a main buffer system (i.e., carbonate buffer system) in the body. However, such bicarbonate dialysis preparations were not sufficient in stability because of carbonates precipitate due to existence of divalent ions such as calcium and magnesium.

Since then, acetate dialysis preparations that contain sodium acetate as an alkalizer were developed to supply hydrogencarbonate ions necessary for correction of acidosis.

After that, given sharp increase of dialysis patients suffering from acetate intolerance induced by use of acetate dialysis preparations, dialysis preparations that contain again sodium hydrogencarbonate as an alkalizer and a little amount of acetic acid (8-12 mEq/L) from necessity of formulation were developed. They are currently mainstream products in the market.

Recently, acetate-free dialysis preparations that contain no acetic acid and contain sodium hydrogencarbonate as the only alkalizer with citric acid-sodium citrate buffering system for a pH controller of dialysates have been suggested, though hydrogencarbonate was conventionally impossible for alkalizing agent.

The present inventors have newly found that above acetate-free dialysis preparations are effective in improvement of aforementioned bone metabolism abnormality developed in chronic renal failure patients receiving blood purification therapy for a long time and completed the invention.

Non-patent literature 1: Quarles L. D. et al., J. Clin. Endcrino. Metab. 75, 145, 1992.

Non-patent literature 2: Coles G. et al., Q. J. Med. 41, 25, 1972.

Non-patent literature 3: Mitch W. et al., Am. J. Kidney Dis. 38, 1337, 2001.

SUMMARY OF THE INVENTION

In the view of the above problems, the present invention has as an object to provide bone metabolism improving agents that improve bone metabolism in a chronic renal failure patient who receives blood purification therapy such as hemodialysis, hemofiltration and hemodiafiltration.

The present invention also has as another object to provide methods for improving bone metabolism in a chronic renal failure patient who receives blood purification therapy such as hemodialysis, hemofiltration and hemodiafiltration, by administration of bone metabolism improving agents provided by the present invention; and more specifically, to provide a method for improving bone metabolism employing a dialysate and/or a substitution fluid that contain above bone metabolism improving agents.

Further, the present invention has as another object to provide methods for blood purification including hemodialysis and hemodiafiltration in a chronic renal failure patient employing dialysates that contain above-mentioned bone metabolism improving agents, and to provide methods for blood purification including hemodiafiltration and hemofiltration in a chronic renal failure patient employing substitution fluids that contain above-mentioned bone metabolism improving agents.

To solve problems in the conventional art, an embodiment of the present invention comprises:

(1) A bone metabolism improving agent comprising no acetic acid and/or an acetate salt and comprising citric acid and/or a citrate salt as electrolytes, and further comprising solely or in combination another/other electrolyte/electrolytes and glucose;

(2) The bone metabolism improving agent of above (1) formulated into a dialysate;

(3) The bone metabolism improving agent of above (1) or (2) formulated into a substitution fluid;

(4) The bone metabolism improving agent of above (1), (2) or (3) characterized in improvement of abnormal bone metabolism induced by adynamic bone disease;

(5) The bone metabolism improving agent of above (1), (2) or (3) characterized in improvement of abnormal bone metabolism induced by bone agenesis in adynamic bone disease;

(6) The bone metabolism improving agent of above (1), (2) or (3) characterized in improvement of abnormal bone metabolism induced by relative hypoparathyroidism in adynamic bone disease;

(7) The bone metabolism improving agent of above (1), (2) or (3) characterized in improvement of abnormal bone metabolism induced by hyperphosphatemia in adynamic bone disease;

(8) The bone metabolism improving agent of above (1), (2) or (3) characterized in improvement of abnormal bone metabolism induced by hypercalcemia in adynamic bone disease; and (9) The bone metabolism improving agent of above (1), (2) or (3) characterized in improvement of abnormal bone metabolism induced by hyper-ionized calcemia in adynamic bone disease.

Another embodiment of the present invention comprises:

(10) A method for improving bone metabolism in a chronic renal failure patient receiving blood purification therapy such as hemodialysis, hemofiltration and hemodiafiltration, by administration of a bone metabolism improving agent of any of above from (1) through (9).

Further, another embodiment of the present invention comprises:

(11) A method for improving bone metabolism in a chronic renal failure patient receiving blood purification therapy such as hemodialysis, hemofiltration and hemodiafiltration, employing a dialysate and/or a substitution fluid that contain the bone metabolism improving agent of above (2) or (3);

(12) A blood purification method including hemodialysis and hemodiafiltration in a chronic renal failure patient employing a dialysate containing the bone metabolism improving agent of above (2); and

(13) A blood purification method including hemodiafiltration and hemofiltration in a chronic renal failure patient employing a substitution fluid containing the bone metabolism improving agent of above (3).

A bone metabolism improving agent provided by the present invention contains citric acid and/or a citrate salt, and more specifically, contains citric acid and/or a citrate salt as electrolytes; and one of efficacies thereof is improvement of bone utilization in a chronic renal failure patient who receives blood purification therapy.

A bone metabolism improving agent provided by the invention corrects blood ionized calcium concentrations through formation of complexes between citric acid and/or a citrate salt and calcium ions. When employed is a conventional dialysate and/or a substitution fluid which produces the same calcium concentrations in the prepared dialysate as those produced by a dialysate and/or a substitution fluid containing a bone metabolism improving agent provided by the invention, blood ionized calcium concentrations increase after dialysis sessions. In contrast, when employed is a dialysate and/or a substitution fluid containing a bone metabolism improving agent provided by the invention, blood ionized concentrations are stable after dialysis sessions, and additionally, blood calcium concentrations as well as bone mineral density do not decline.

In chronic renal failure patients with adynamic bone disease (bone agenesis) under a blood purification therapy, inhibition of elevation of blood ionized calcium concentrations stimulates parathyroid glands to increase secretion of parathyroid hormone, and as a result, adynamic bone disease is improved.

Moreover, a bone metabolism improving agent provided by the invention corrects abnormal bone metabolism by inhibiting hypofunction of parathyroid glands which control bone turnover.

Hence, it is a great advantage of the present invention that a bone metabolism improving agent provided by the invention improves renal osteodystrophy and especially adynamic bone disease in chronic renal failure patients to avoid onset of complications such as decreased bone mineral density and contribute to improvement of their QOL and prognosis.

Conventionally, use of low-calcium-concentration preparations has been recommended for patients developing adynamic bone disease. In a bone metabolism improving agent provided by the invention, calcium concentrations are high, while ionized calcium concentrations are low. Therefore, a bone metabolism improving agent provided by the invention carries few risks of hypocalcemia unlike conventional low-calcium-concentration dialysis preparations.

For example, as shown in the experimental results below, the calcium concentration (total calcium content) of a bone metabolism improving agent provided by the invention is 3 mEq/L and the ionized calcium concentration of the same is 1.05 mmol/L, which is considered to be effective in improvement of bone metabolism in adynamic bone disease.

The aforementioned are some of distinctive features of the present invention.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
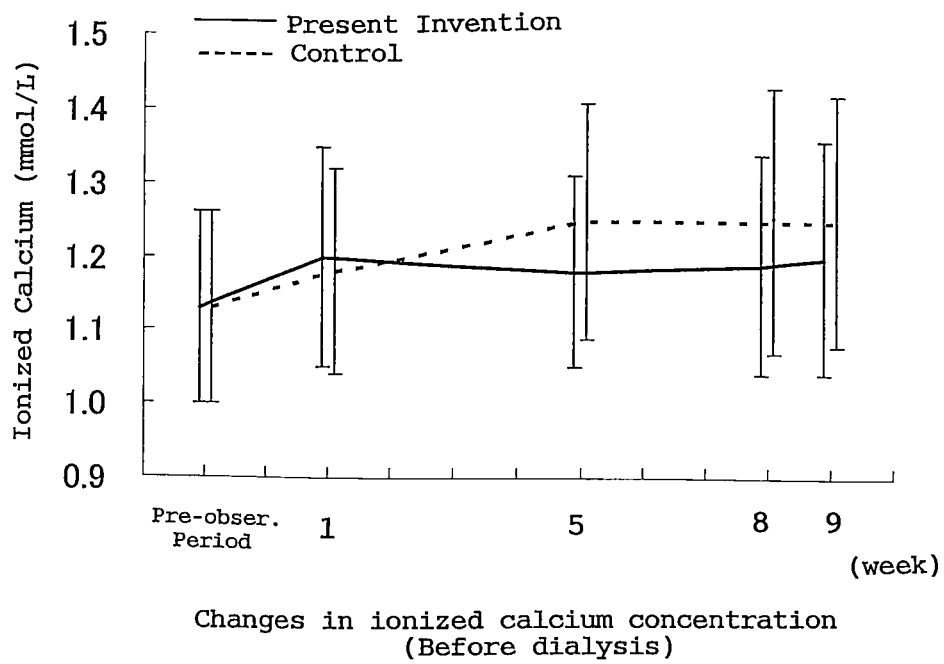
FIG. 1 shows the changes of ionized calcium concentrations before dialysis in Example 1.

Other features of the invention will become apparent in the course of the following descriptions of exemplary embodiments which are given for illustration of the invention and are not intended to be limiting thereof.

As abovementioned, a bone metabolism improving agent provided by the present invention contains citric acid and/or a citrate salt.

More specifically, a bone metabolism improving agent provided by the present invention is characterized in that it does not contain acetic acid and/or an acetate salt and contains citric acid and/or a citrate salt as electrolytes, and additionally, contains another/other electrolyte/electrolytes and glucose solely or in combination.

Hence, preferably, a bone metabolism improving agent provided by the invention is administered in a formulation of a dialysate or a substitution fluid. A preferable embodiment of such a dialysate or a substitution fluid is a bicarbonate dialysate or a bicarbonate substitution fluid which contains sodium bicarbonate of bicarbonate ions as alkalizer.

In view of the above, a preferable embodiment of a bone metabolism improving agent provided by the present invention is a dialysate so-called dialysis preparation "A" comprising electrolytes, pH adjusting agents and/or glucose; the dialysis preparation "A" is diluted, for administration, with a diluting water or, preferably, with a so-called dialysis preparation "B" comprising sodium hydrogencarbonate of bicarbonate irons.

Another preferable embodiment of a bone metabolism improving agent provided by the present invention is a substitution fluid so-called dialysis preparation "B" comprising electrolytes, pH adjusting agents and/or glucose; the dialysis preparation "B" is mixed, for administration, with a dialysis preparation "A" comprising electrolytes, pH adjusting agents and sodium hydrogencarbonate.

Preferable electrolytes used in a bone metabolism improving agent provided by the present invention in addition to citric acid and/or a citrate salt such as sodium citrate include, for example, sodium chloride, potassium chloride, magnesium chloride, calcium chloride, sodium lactate, potassium lactate, calcium lactate, calcium succinate and calcium gluconate. Especially, preferable electrolytes include sodium chloride, potassium chloride, calcium chloride, magnesium chloride and sodium citrate.

In addition to above-mentioned components, a bone metabolism improving agent provided by the present invention contains glucose and pH adjusting agents to suitably control the pH of a dialysate and/or a substitution fluid after preparation.

Preferable pH adjusting agents include citric acid, lactic acid, hydrochloric acid, malic acid, succinic acid, ascorbic acid, tartaric acid and sodium hydroxide. Especially, preferable pH adjusting agents include citric acid and succinic acid.

Accordingly, a bone metabolism improving agent provided by the present invention contains above-mentioned components preferably at the concentrations as described below when suitably diluted and mixed to be a bicarbonate dialysate or a bicarbonate substitution fluid.

| | |
|---|---|
| Sodium ion | 120-150 mEq/L |
| Potassium ion | 0-5 mEq/L |
| Calcium ion | 0-5 mEq/L |
| Magnesium ion | 0-2 mEq/L |
| Chloride ion | 55-135 mEq/L |
| Bicarbonate ion | 20-45 mEq/L |
| Citrate ion | 0.02-5 mEq/L |
| Glucose | 0-3.0 g/L |

When calcium ions are included as an electrolyte in a bone metabolism improving agent provided by the present invention, insoluble compounds are produced because of the existence of citric acid and/or a citrate salt such as sodium citrate. However, production of such insoluble compounds is prevented by controlling a pH of agent at lower levels with citric acid.

Furthermore, use of citric acid suppresses generation of precipitates. When electrolytes in a dialysis preparation "A" or a substitution fluid "B" are mixed with sodium bicarbonate of bicarbonate irons in a dialysis preparation "B" or a substitution fluid "A", reaction between bicarbonate ions and calcium or magnesium ions produces insoluble metal carbonates. Therefore, these "A" and "B" are mixed and diluted just before use as a dialysate for artificial kidney. An advantage of the present invention is that citric acid's precipitate-suppressing effect prolongs the stability of dialysate.

According to the present invention, preferably citric acid and/or a citrate salt are contained in a bone metabolism improving agent in the amount that allows a pH of prepared dialysate to range about between 2.2 and 2.9, and that allows a citrate ion concentration to usually range between 0.02 and 5 mEq/L as described above.

Moreover, against conventional dialysis preparation "A"s and substitution fluid "B"s containing acetic acid, a bone metabolism improving agent provided by the present invention is characterized by acetic-acid free formulation. Hence, it is another advantage of the present invention that a dialysate and/or a substitution fluid formulated with a bone metabolism improving agent provided by the present are physiologically more compatible because sodium bicarbonate is used as the only alkalizer.

A bone metabolism improving agent provided by the present invention is capable of correcting blood ionized calcium concentrations without decrease in bone mineral density owing to action of citric acid and/or a citrate salt contained therein, and for enhancement of effectiveness, is preferably free of any substances that affect calcium ionization rates such as acetic acid.

A bone metabolism improving agent provided by the present invention is effective in improvement of bone metabolism in chronic renal failure patients with i-PTH levels at 180 pg/mL or less and markedly effective in chronic renal failure patients with i-PTH levels at 60 pg/mL or less but, in contrast, practically no effect of bone metabolism improvement was demonstrated in chronic renal failure patients with i-PTH levels at 180 pg/mL or more. This is one of especially unique features of a bone metabolism improving agent provided by the present invention.

An embodiment of aforementioned unique bone metabolism improving agent provided by the present invention is used in formulation of a dialysate and/or a substitution fluid.

EXAMPLES

Having generally described this invention, a further understanding can be obtained by reference to certain specific examples which are provided herein for purposes of illustration only and are not intended to be limiting unless otherwise specified.

Example 1

Effects of a Dialysis Preparation Provided by the Invention on Bone Metabolism in Chronic Renal Failure Patients Chronic renal failure patients who need hemodialysis treatment were dialyzed with a dialysis preparation (an acetic acid-free dialysis preparation) which has bone-metabolism improving efficacy provided by the invention and with a control dialysis preparation (a commercial bicarbonate dialysis preparation containing acetic acid). Then, effects on bone metabolism were evaluated.

Fully-informed consent was obtained from patients prior to the administration.

[Experimental Design]

An open-label, crossover (two periods, two groups), comparative study was performed according to the experimental design in Table 1.

TABLE 1

|  | Pre-observation Period | Trial Period First Period (8 weeks) | Trial Period Second Period (8 weeks) | Post-observation Period |
|---|---|---|---|---|
| Group A | Commercial dialysates (2 weeks) | A dialysate provided by the invention | A control dialysate | Commercial dialysates (One day) |
| Group B |  | A control dialysate | A dialysate provided by the invention |  |

Compositions of the dialysate provided by the invention and the control dialysate used for administration were as follows.

TABLE 2

|  | Concentration (mEq/L) | |
|---|---|---|
| Component | Dialysate Provided by the Invention | Commercial Dialysate |
| Sodium | 140 | 140 |
| Potassium | 2.0 | 2.0 |
| Calcium | 3.0 | 3.0 |
| Magnesium | 1.0 | 1.0 |
| Chlorine | 111 | 111 |
| Hydrogencarbonate | 35 | 25 |
| Acetic acid | — | 10 |
| Citric acid | 1.4 | — |
| Sodium citrate | 0.3 | — |
| Glucose (mg/dL) | 150 | 100 |

The actual values of ionized calcium concentrations of both dialysates were as follows, respectively.

The dialysate provided by the invention: 1.01 mmol/L
The control dialysate: 1.35 mmol/L
(Measurement Device: i-STAT of i-STAT Corporation)

The calcium content (total calcium) of the dialysate provided by the invention was 3 mEq/L equal to that of the control dialysate; however, the ionized calcium concentration of the dialysate provided by the invention was lower than that of the control dialysate.

[Experimental Means]

The subject group A consisted of 36 male and 19 female patients—in total 55 patients—(age: 61.6±10.2). The subject group B consisted of 29 male and 24 female patients—in total 53 patients—(age: 60.7±8.8).

Primary disease of most patients in both groups was chronic renal failure (chronic glomerulonephritis), and the duration of dialysis session was between 4 and 5 hours in most cases.

Dialysis was performed three times a week taking between 3 and 5 hours per session.

After 2-week pre-observation period receiving dialysis with the commercial dialysates from Dialysate-a to Dialysate-d (bicarbonate dialysates containing acetic acid), patients in Group A received dialysis with the dialysate provided by the invention and patients in Group B received dialysis with the control dialysate during the first trial period (8 weeks). Then, during the subsequent second trial period (8 weeks), patients in Group A received dialysis with the control dialysate and patients in Group B received the dialysate provided by the invention. After the trial period, patients received dialysis with the same commercial dialysates from Dialysate-a to Dialysate-d as used in the pre-observation period for one-day post-observation period.

For evaluation of bone metabolism improvement, changes in blood ionized calcium concentrations, "corrected" serum calcium concentrations and i-PTH concentrations were assayed.

The commercial dialysates used in the pre-observation period were from Dialysate-a to Dialysate-d with components shown in Table 3.

TABLE 3

|  | Prescription of Commercial Dialysates (mEq/L) | | | |
|---|---|---|---|---|
| Component | Dialysate-a | Dialysate-b | Dialysate-c | Dialysate-d |
| Sodium | 140 | 140 | 143 | 140 |
| Potassium | 2.0 | 2.0 | 2.0 | 2.0 |
| Calcium | 3.0 | 3.0 | 2.5 | 2.5 |

TABLE 3-continued

| | Prescription of Commercial Dialysates (mEq/L) | | | |
|---|---|---|---|---|
| Component | Dialysate-a | Dialysate-b | Dialysate-c | Dialysate-d |
| Magnesium | 1.0 | 1.0 | 1.0 | 1.0 |
| Chlorine | 111 | 110 | 112 | 112.5 |
| Hydrogencarbonate | 25 | 30 | 27.5 | 25 |
| Acetic acid | 10 | 6 | 9 | 8 |
| Glucose (mg/dL) | 100 | 100 | 100 | 150 |

[Results and Discussion]

Figure 2:
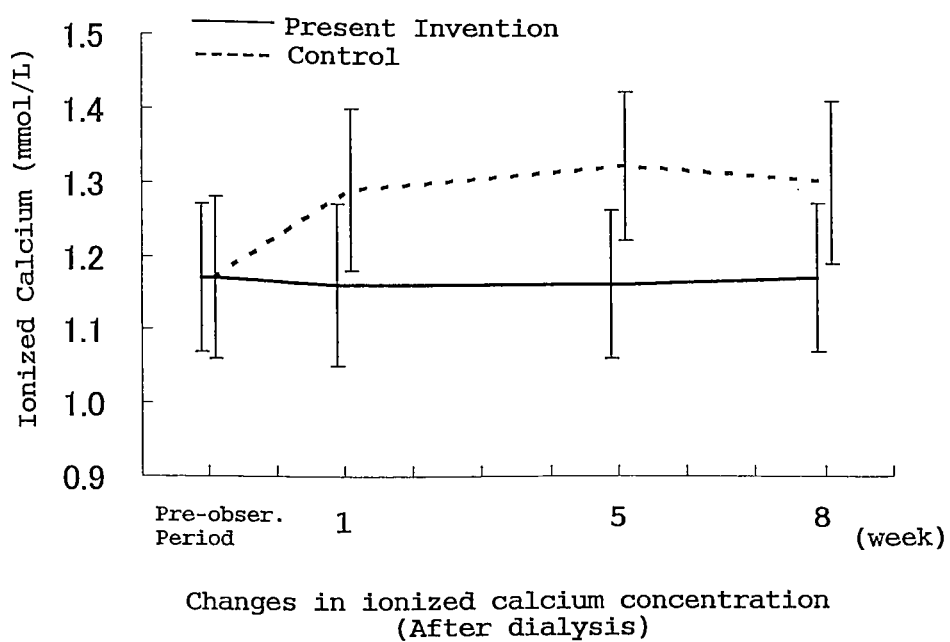
FIG. 2 shows the changes of ionized calcium concentrations after dialysis in Example 1.

Changes in ionized calcium concentrations before and after dialysis in the trial period are shown in FIGS. 1 and 2, respectively.

As shown in the results in the Figures, ionized calcium concentrations in the patients dialyzed with the dialysate provided by the invention changed within the normal range both before and after dialysis and were maintained lower than those in the patients dialyzed with the control dialysate.

Ionized calcium concentrations before the first dialysis session in the $8^{th}$ week of trial period were 1.192±0.150 mmol/L in the group dialyzed with the dialysate provided by the invention and 1.253±0.172 mmol/L in the control group. Ionized calcium concentrations after the session were 1.168±0.101 mmol/L in the group dialyzed with the dialysate provided by the invention and 1.307±0.113 mmol/L in the control group. Ionized calcium concentrations in the control group were higher than those in the group dialyzed with the dialysate provided by the invention both before and after the dialysis session.

Corrected serum calcium concentrations before the first dialysis session in the $8^{th}$ week of trial period were 9.66±0.80 mg/dL in the group dialyzed with the dialysate provided by the invention and 9.71±0.85 mg/dL in the control group, almost the same in both groups. Corrected serum calcium concentrations after the session were 9.72±0.38 mg/dL in the group dialyzed with the dialysate provided by the invention and 9.91±0.41 mg/dL in the control group. Serum calcium concentrations in the group dialyzed with the dialysate provided by the invention were slightly lower than those in the control group.

As a result, blood ionized calcium concentrations after dialysis sessions in the control group changed at higher levels than those in the group dialyzed with the dialysate provided by the invention and exceeded the upper limit of normal range in the $5^{th}$ and $8^{th}$ weeks of trial period; in contrast, the average blood ionized calcium concentrations after dialysis sessions in the group dialyzed with the dialysate provided by the invention were kept within the normal range (1.05-1.30 mmol/L).

According to the above, because blood ionized calcium concentrations after dialysis sessions in the group dialyzed with the dialysate provided by the invention were maintained within the normal range against the control group, it is indicated that the dialysate provided by the invention is an excellent dialysis preparation capable of correcting blood ionized calcium concentrations to the levels closer to normal.

Furthermore, while the control dialysate is known to enhance the probability of elevating corrected serum calcium concentrations after dialysis, elevation of corrected serum calcium concentrations in the group dialyzed with the dialysate provided by the invention was suppressed at lower levels compared to the control group. Therefore, the dialysate provided by the invention is judged to have ideal effects on calcium metabolism unlike the control dialysate.

According to the "Guidelines for Treatment of Secondary Hyperparathyroidism in Dialysis Patients" published by the Japan Society for Dialysis Therapy (Journal of JSDT 39 (10): 1435-1455, 2006), for "management of parathyroid function and assessment of bone metabolism", function of parathyroid glands are usually evaluated by i-PTH values and i-PTH values determine bone metabolism condition.

Therefore, changes of i-PTH values were investigated for bone metabolism condition in the above experiment. In patients with lower i-PTH levels (less than 60 pg/mL) than the management standard according to the guidelines (60-180 pg/mL) in the pre-observation period, changes of i-PTH levels in the $9^{th}$ week of trial period under dialysis treatment with the dialysate provided by the invention and the control dialysate from the i-PTH levels in the pre-observation period were evaluated. The results are shown in FIGS. 3 and 4.

Figure 3:
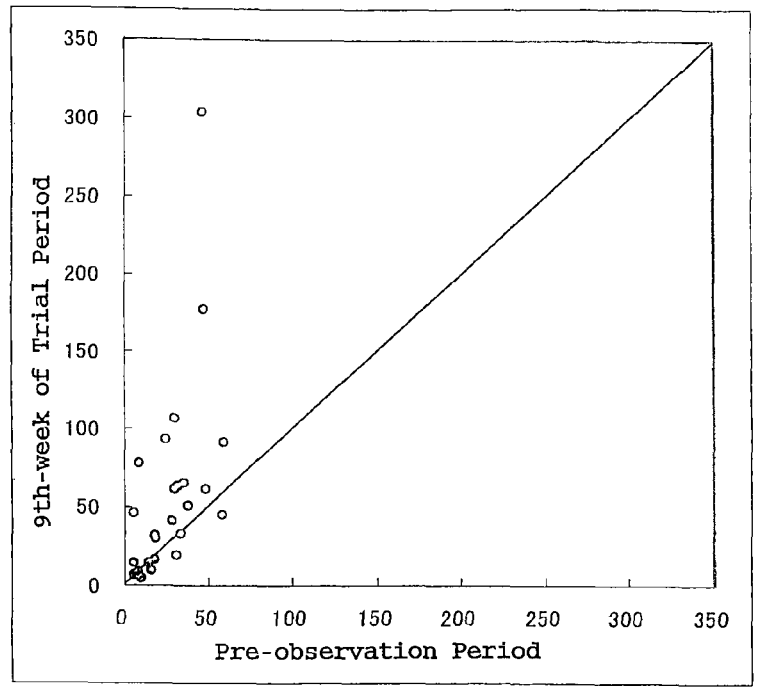
FIG. 3 shows the changes of i-PTH levels in the group dialyzed with the dialysate provided by the invention in Example 1.
Figure 4:
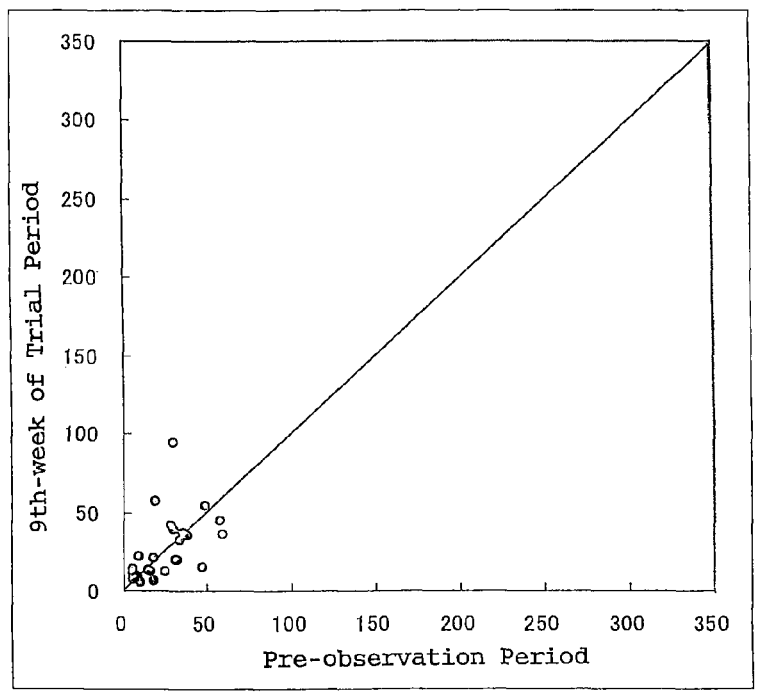
FIG. 4 shows the changes of i-PTH levels in the group dialyzed with the control dialysate in Example 1.

As indicated by changes shown in FIGS. 3 and 4, in 21 cases who were assumed to have adynamic bone disease with i-PTH levels lower than 60 pg/mL, elevation of i-PTH levels was observed in the group dialyzed with the dialysate provided by the invention, but practically no change of i-PTH levels was observed in the group dialyzed with the control dialysate (20 cases).

From these results, the dialysate provided by the invention is judged to demonstrate bone metabolism improving efficacy in adynamic bone disease through correction of blood ionized calcium concentrations.

In addition, patients were divided into 3 groups of one with i-PTH lower than the guidelines' management standard range (60-180 pg/mL), another with i-PTH within the standard range and a third with i-PTH exceeding the standard range. Then, ionized calcium concentrations, corrected serum calcium concentrations and i-PTH levels in the $9^{th}$ week of trial period under dialysis treatment with the dialysate provided by the invention and the control dialysate are shown in Table 4.

TABLE 4

| | | Ionized Ca Concentration | | | | Corrected Ca Concentration | | | | i-PTH Concentration | | | |
|---|---|---|---|---|---|---|---|---|---|---|---|---|---|
| | | Dialysate by Invention | | Control Dialysate | | Dialysate by Invention | | Control Dialysate | | Dialysate by Invention | | Control Dialysate | |
| Range | | Pre-observation | 9th week | Pre-observation | 9th week | Pre-observation | 9th week | Pre-observation | 9th week | Pre-observation | 9th week | Pre-observation | 9th week |
| i-PTH: under 60 | Mean | 1.15 | 1.16 | 1.15 | 1.23 | 9.83 | 9.62 | 9.83 | 9.98 | 27.4 | 55.9 | 27.3 | 27.7 |
| | SD | 0.16 | 0.11 | 0.17 | 0.17 | 0.47 | 0.67 | 0.48 | 0.99 | 16.6 | 64.1 | 17 | 21.9 |
| | n | 21 | 21 | 20 | 20 | 21 | 21 | 20 | 20 | 21 | 21 | 20 | 20 |
| i-PTH: 60-180 | Mean | 1.09 | 1.16 | 1.09 | 1.21 | 9.32 | 9.51 | 9.32 | 9.42 | 108.8 | 125.6 | 108.8 | 103.8 |
| | SD | 0.12 | 0.17 | 0.12 | 0.18 | 0.57 | 0.84 | 0.57 | 0.82 | 32.2 | 61.5 | 32.2 | 52 |
| | n | 37 | 37 | 37 | 37 | 37 | 37 | 37 | 37 | 37 | 37 | 37 | 37 |

TABLE 4-continued

| | | Ionized Ca Concentration | | | | Corrected Ca Concentration | | | | i-PTH Concentration | | | |
|---|---|---|---|---|---|---|---|---|---|---|---|---|---|
| | | Dialysate by Invention | | Control Dialysate | | Dialysate by Invention | | Control Dialysate | | Dialysate by Invention | | Control Dialysate | |
| Range | | Pre-obser-vation | 9th week | Pre-obser-vation | 9th week | Pre-obser-vation | 9th week | Pre-obser-vation | 9th week | Pre-obser-vation | 9th week | Pre-obser-vation | 9th week |
| i-PTH: over 180 | Mean | 1.16 | 1.25 | 1.16 | 1.29 | 9.61 | 9.81 | 9.61 | 9.86 | 287.3 | 261.9 | 287.3 | 229.1 |
| | SD | 0.12 | 0.15 | 0.12 | 0.15 | 0.73 | 0.83 | 0.73 | 0.91 | 109.6 | 143.3 | 109.6 | 136.6 |
| | n | 43 | 43 | 43 | 43 | 43 | 43 | 43 | 43 | 43 | 43 | 43 | 43 |

In the group with i-PTH under 60 pg/mL in the pre-observation period, blood ionized calcium concentrations of patients dialyzed with the dialysate provided by the invention did not change between the pre-observation period and the 9$^{th}$ week of trial period, while their i-PTH levels were observed to increase. In contrast, blood ionized calcium concentrations of patients dialyzed with the control dialysate were elevated, while their i-PTH levels were not observed to increase.

In the group with i-PTH within the management standard range (60-180 pg/mL), i-PTH levels of patients dialyzed with the dialysate provided by the invention were slightly elevated. However, i-PTH levels of both groups dialyzed with the dialysate provided by the invention and the control dialysate were maintained within the management standard range.

In the group with i-PTH 180 pg/mL or above, i-PTH levels of both groups dialyzed with the dialysate provided by the invention and the control dialysate were not observed to increase.

According to the above, it is indicated that the dialysate provided by the invention improves bone metabolism in adynamic bone disease subjects with i-PTH under 60 pg/mL through acceleration of PTH secretion and does not increase i-PTH secretion—that is, does not give any adverse effects on bone metabolism—in subjects with i-PTH within the management standard range or above.

Preparation Examples (1) Dialysate

| Preparation "A" (component and amount per 10 L) | |
|---|---|
| Sodium chloride | 2,148.0 g |
| Potassium chloride | 52.0 g |
| Calcium chloride | 77.0 g |
| Magnesium chloride | 36.0 g |
| Glucose | 525.0 g |
| Citric acid | 34.3 g |
| Sodium citrate | 10.3 g |

| Preparation "B" (component and amount per 12.6 L) | |
|---|---|
| Sodium hydrogencarbonate | 1,030.0 g |

(2) Substitution Fluid

| Preparation "A" (component and amount per 1,010 mL) | |
|---|---|
| Sodium chloride | 12.34 g |
| Potassium chloride | 0.30 g |
| Sodium hydrogencarbonate | 5.94 g |

| Preparation "B" (component and amount per 1,010 mL) | |
|---|---|
| Calcium chloride | 519.8 mg |
| Magnesium chloride | 205.4 mg |
| Glucose | 2.02 g |
| Citric acid | 198.0 mg |
| Sodium citrate | 59.4 mg |

As aforementioned, according to the present invention, an acetic acid- and/or acetate salt-free bone metabolism improving agent containing citric acid and/or a citrate salt has effects of improving bone metabolism in adynamic bone disease through correction of blood ionized calcium concentrations in chronic renal failure patients receiving blood purification therapy.

Hence, a dialysis preparation provided by the present invention has great medical advantages for its contribution to improvement of QOL and prognosis of patients through improvement of renal osteodystrophy and especially adynamic bone disease in chronic renal failure patients and also through avoidance of risks of complications such as decreased bone mineral density.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method of improving abnormal bone metabolism induced by adynamic bone disease, comprising:
    administering a bone metabolism improving agent to a subject in need of such improvement;
    wherein:
    the bone metabolism improving agent is a dialysate and/or a substitution fluid and comprises:
    citric acid and/or citrate salt; and
    at least one of an additional electrolyte and glucose; and
    the bone metabolism improving agent is free of acetic acid and acetate salts, and has a high calcium concentration and a low ionized calcium concentration, the high calcium concentration is a concentration of about 3 mEq/L, and the low ionized calcium concentration is a concentration of about 1.05 mmol/L.

2. A method of claim 1, wherein the abnormal bone metabolism is abnormal bone metabolism induced by bone agenesis in adynamic bone disease.

3. A method of claim 1, wherein the abnormal bone metabolism is abnormal bone metabolism induced by relative hypoparathyroidism in adynamic bone disease.

4. A method of claim 1, wherein the abnormal bone metabolism is abnormal bone metabolism induced by hyperphosphatemia in adynamic bone disease.

5. A method of claim 1, wherein the abnormal bone metabolism is abnormal bone metabolism induced by hypercalcemia in adynamic bone disease.

6. A method of claim 1, wherein the abnormal bone metabolism is abnormal bone metabolism induced by hyperionized calcemia in adynamic bone disease.

7. The method of claim 1, wherein the bone metabolism improving agent is a dialysate.

8. The method of claim 1, wherein the bone metabolism improving agent is a substitution fluid.

9. A method for improving bone metabolism in a chronic renal failure patient receiving blood purification therapy, comprising:
administering the bone metabolism improving agent to a subject in need of such improvement;
wherein:
the bone metabolism improving agent is a dialysate and/or a substitution fluid and comprises:
citric acid and/or a citrate salt; and
at least one of an additional electrode and glucose; and
the bone metabolism improving agent is free of acetic acid and acetate salts, and has a high calcium concentration and a low ionized calcium concentration, the high calcium concentration is concentration of about 3 mEq/L and the low ionized calcium concentration is a concentration of about 1.05 mmol/L.

10. The method of claim 9, wherein the blood purification therapy comprises at least one of hemodialysis, hemofiltration and hemodiafiltration.

11. The method of claim 9, wherein the blood purification therapy comprises hemodialysis.

12. The method of claim 9, wherein the blood purification therapy comprises hemofiltration.

13. A method for improving bone metabolism in a chronic renal failure patient receiving blood purification therapy, comprising:
administering the dialysate to a subject in need of such improvement;
wherein:
the dialysate comprises;
citric acid and/or a citrate salt; and
at least one of an additional electrolyte and glucose; and
the dialysate is free of acetic acid and acetate salts, and has a high calcium concentration and a low ionized calcium concentration, the high calcium concentration is a concentration of about 3 mEq/L and the low ionized calcium concentration is a concentration of about 1.05 mmol/L.

14. The method of claim 13, wherein the blood purification therapy comprises at least one of hemodialysis, hemofiltration and hemodiafiltration.

15. The method of claim 13, wherein the blood purification therapy comprises hemodialysis.

16. The method of claim 13, wherein the blood purification therapy comprises hemodiafiltration.

17. A method for improving bone metabolism in a chronic renal failure patient receiving blood purification therapy, comprising:
administering the substitution fluid to a subject in need of such improvement;
wherein:
the substitution fluid comprises:
citric acid and/or a citrate salt; and
at least one of an additional electrolyte and glucose; and
the substitution fluid is free of acetic acid and acetate salts, and has a high calcium concentration and a low ionized calcium concentration, the high calcium concentration is a concentration of about 3 mEq/L and the low ionized calcium concentration is a concentration of about 1.05 mmol/L.

18. The method of claim 17, wherein the blood purification therapy comprises at least one of hemodialysis, hemofiltration and hemodiafiltration.

19. The method of 17, wherein the blood purification therapy comprises hemofiltration.

20. The method of claim 17, wherein the blood purification therapy comprises hemodiafiltration.

* * * * *